US010767876B2

(12) United States Patent
Kelly et al.

(10) Patent No.: US 10,767,876 B2
(45) Date of Patent: Sep. 8, 2020

(54) SYSTEMS AND METHODS FOR MONITORING AIR QUALITY AND EVENTS LIKELY TO AFFECT AIR QUALITY, AND TAKING REMEDIAL ACTION

(71) Applicant: KONINKLIJKE PHILIPS N.V., Eindhoven (NL)

(72) Inventors: Declan Patrick Kelly, Eindhoven (NL); Cornelis Reinder Ronda, Eindhoven (NL); Xiaoming Zhou, Eindhoven (NL); Amanda Zhao, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 505 days.

(21) Appl. No.: 15/536,781

(22) PCT Filed: Dec. 21, 2015

(86) PCT No.: PCT/EP2015/080867
§ 371 (c)(1),
(2) Date: Jun. 16, 2017

(87) PCT Pub. No.: WO2016/102510
PCT Pub. Date: Jun. 30, 2016

(65) Prior Publication Data
US 2017/0328591 A1 Nov. 16, 2017

(30) Foreign Application Priority Data

Dec. 24, 2014 (WO) ................ PCT/CN2014/094815
Jan. 30, 2015 (EP) ..................................... 15153324

(51) Int. Cl.
*G01H 3/00* (2006.01)
*F24F 3/16* (2006.01)
(Continued)

(52) U.S. Cl.
CPC ........ *F24F 3/1603* (2013.01); *B01D 46/0086* (2013.01); *B01D 46/46* (2013.01);
(Continued)

(58) Field of Classification Search
CPC .............. F24F 11/30; F24F 11/56; G01H 3/00
See application file for complete search history.

(56) References Cited

U.S. PATENT DOCUMENTS 7,837,958 B2 * 11/2010 Crapser ................... A47L 11/24
15/319
9,989,507 B2 * 6/2018 Benn ...................... G01K 13/00
(Continued)

FOREIGN PATENT DOCUMENTS

DE        20003158 U     6/2000
EP         1050332 A2    11/2000
(Continued)

*Primary Examiner* — Jamel E Williams

(57) ABSTRACT

In various embodiments, an air quality-monitoring system (100) may include at least one sensor (106) configured to detect operation of a mechanism (110) within or at a boundary of an indoor environment. The mechanism may be external to an air purifier (102) associated with the indoor environment. The system may include a persistent memory (124) for storing data about the indoor environment observed by the at least one sensor (106). A controller (104) may be communicatively coupled with the at least one sensor and configured to: assemble the data into an air quality profile associated with that environment; determine, based on a signal from the at least one sensor and on the air quality profile, a likelihood that operation of the mechanism will cause a measure of air quality within the indoor environment to fail one or more air quality criteria; and selectively provide, based on the likelihood, an indication that operation of the mechanism will cause the measure of air quality within the indoor environment to fail the one or more air quality criteria.

15 Claims, 5 Drawing Sheets

(51) Int. Cl.
  *F24F 11/30*    (2018.01)
  *B01D 46/00*    (2006.01)
  *B01D 46/46*    (2006.01)
  *G01N 33/00*    (2006.01)
  *F24F 11/56*    (2018.01)
  *F24F 110/66*   (2018.01)
  *F24F 110/52*   (2018.01)
  *F24F 110/64*   (2018.01)
  *F24F 110/50*   (2018.01)
  *F24F 110/60*   (2018.01)
  *F24F 110/62*   (2018.01)

(52) U.S. Cl.
  CPC .............. *F24F 11/30* (2018.01); *G01H 3/00* (2013.01); *G01N 33/0073* (2013.01); *F24F 11/56* (2018.01); *F24F 2110/50* (2018.01); *F24F 2110/52* (2018.01); *F24F 2110/60* (2018.01); *F24F 2110/62* (2018.01); *F24F 2110/64* (2018.01); *F24F 2110/66* (2018.01); *F24F 2221/18* (2013.01)

(56) References Cited

U.S. PATENT DOCUMENTS

| | | | |
|---|---|---|---|
| 10,345,933 B2 * | 7/2019 | Sasaki | F24F 11/30 |
| 2002/0078830 A1 * | 6/2002 | Chung | B01D 46/008 |
| | | | 96/424 |
| 2005/0224069 A1 * | 10/2005 | Patil | F24C 15/2021 |
| | | | 126/299 D |
| 2006/0059872 A1 | 3/2006 | Lee | |
| 2008/0091284 A1 * | 4/2008 | Sugiyama | H02J 3/14 |
| | | | 700/90 |
| 2008/0206092 A1 * | 8/2008 | Crapser | A47L 11/24 |
| | | | 422/5 |
| 2009/0298192 A1 | 12/2009 | Parham | |
| 2010/0199513 A1 | 8/2010 | Sanders | |
| 2010/0225493 A1 | 9/2010 | Zishaan | |
| 2011/0076185 A1 * | 3/2011 | Hammond | A61L 9/03 |
| | | | 422/3 |
| 2011/0125329 A1 * | 5/2011 | Oswald | G05B 15/02 |
| | | | 700/276 |
| 2011/0284091 A1 * | 11/2011 | Livchak | F24C 15/2021 |
| | | | 137/2 |
| 2012/0151889 A1 | 6/2012 | Horey | |
| 2012/0203461 A1 | 8/2012 | Yiu | |
| 2012/0256009 A1 * | 10/2012 | Mucignat | G05D 23/1905 |
| | | | 236/1 C |
| 2014/0207282 A1 * | 7/2014 | Angle | G05B 15/02 |
| | | | 700/257 |
| 2015/0077737 A1 * | 3/2015 | Belinsky | G01N 21/53 |
| | | | 356/51 |
| 2015/0108119 A1 * | 4/2015 | Armstrong | H05B 6/6447 |
| | | | 219/720 |
| 2015/0153317 A1 * | 6/2015 | Krebs | G01N 33/0062 |
| | | | 96/397 |
| 2018/0372330 A1 * | 12/2018 | Ronda | G05B 15/02 |

FOREIGN PATENT DOCUMENTS

| | | |
|---|---|---|
| JP | H01180215 | 7/1980 |
| JP | 2000304314 | 11/2000 |
| JP | 2006098007 | 4/2006 |
| JP | 2006200818 | 8/2006 |
| JP | 2006200818 A | 8/2006 |
| JP | 2010043854 | 2/2010 |
| JP | 2010043854 A | 2/2010 |
| JP | 2010254001 | 11/2010 |
| JP | 2010254001 A | 11/2010 |
| JP | 2011162096 | 8/2011 |
| JP | 2011162096 A | 8/2011 |
| JP | 2013180178 | 9/2013 |
| JP | 2013180178 A | 9/2013 |
| KR | 20080086669 A | 9/2008 |
| WO | 02063294 A2 | 8/2002 |

* cited by examiner

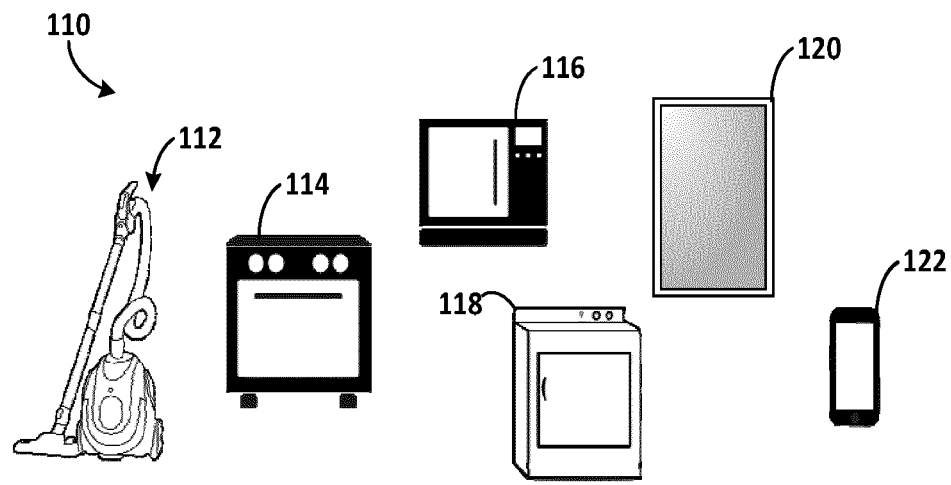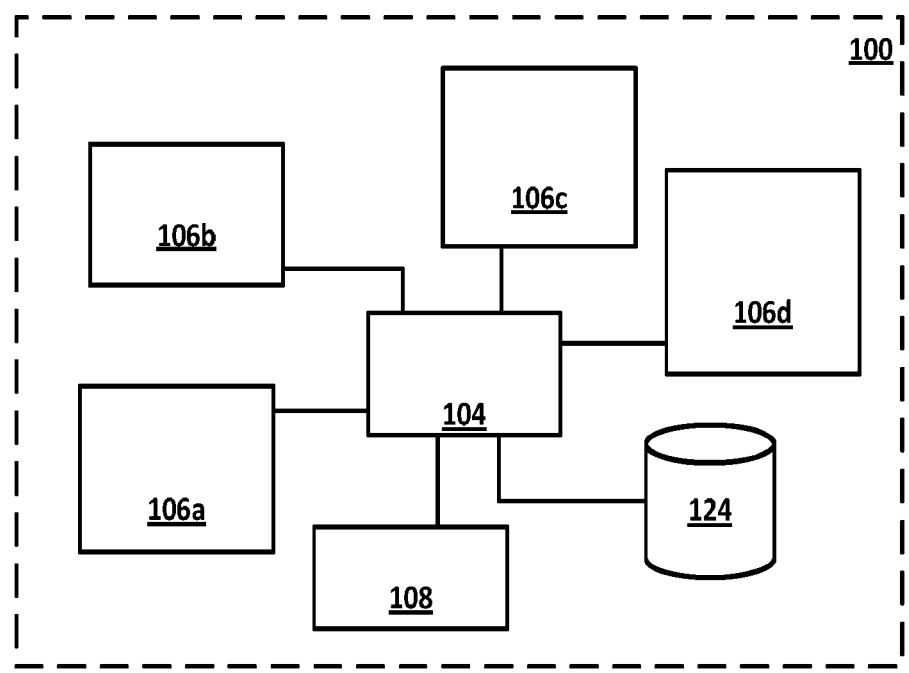
Fig. 1
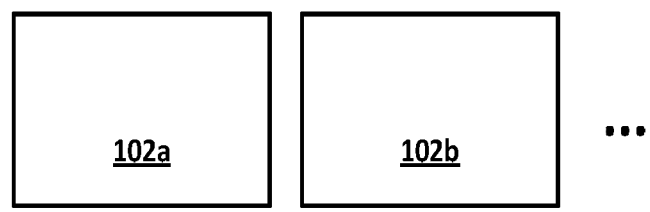

SYSTEMS AND METHODS FOR MONITORING AIR QUALITY AND EVENTS LIKELY TO AFFECT AIR QUALITY, AND TAKING REMEDIAL ACTION

This application is the U.S. National Phase application under 35 U.S.C. § 371 of International Application No. PCT/EP2015/080867, filed on Dec. 21, 2015, which claims the benefit of International Application No. PCT/CN2014/094815 filed on Dec. 24, 2014 and International Application No. 15153324.7 filed on Jan. 30, 2015. These applications are hereby incorporated by reference herein.

FIELD OF THE INVENTION

The present invention is directed generally to air purification. More particularly, various inventive methods and apparatus disclosed herein relate to monitoring air quality and purifying air in response to likely changes in air quality.

BACKGROUND OF THE INVENTION

Air quality in an environment may change before, during, and after various events. For example, in an indoor environment such as an office or one or more rooms of a home or apartment, levels of some types of pollutants may increase when certain appliances (e.g., vacuum cleaners, washers, dryers, stoves, ovens, grills, griddles, microwaves, etc.) are operated. Levels of some types of pollutants may increase when the indoor environment is exposed to an external environment by, for example, a window or door being opened. For example, pollutants typically associated with outdoor sources (e.g., some types of particles, smog) may be present at higher levels in a home when one or more windows are open. Some types of pollutants may be present at increased levels when an occupant is performing an activity that may introduce pollutants into the indoor environment, such as smoking, painting, etc. Operating an air purifier without regard to the changes in air quality caused by these various events may lead to overconsumption of power and/or unnecessary wear and tear on the air purifier and/or one or more incorporated air filters. Even operating an air purifier in response to detected changes in air quality caused by these various events may not be sufficient to prevent durations of unacceptable air quality.

SUMMARY OF THE INVENTION

The present disclosure is directed to inventive methods and apparatus for monitoring air quality, making recommendations, and taking remedial action when necessary. In various embodiments, an air quality-monitoring system may include at least one sensor configured to detect operation of a mechanism within or at a boundary of an indoor environment. The mechanism may be external to an air purifier associated with the indoor environment. The system may include a persistent memory for storing data about the indoor environment observed by the at least one sensor. The system may also include a controller communicatively coupled with the at least one sensor and configured to: assemble the data into an air quality profile associated with that environment; determine, based on a signal from the at least one sensor and on the air quality profile, a likelihood that operation of the mechanism will cause a measure of air quality within the indoor environment to fail one or more air quality criteria; and selectively provide, based on the likelihood, an indication that operation of the mechanism will cause the measure of air quality within the indoor environment to fail the one or more air quality criteria.

In some embodiments, the controller may be further configured to selectively transmit the indication to the air purifier. The indication may be configured to cause the air purifier to take remedial action to prevent the measure of air quality within the indoor environment from failing the one or more air quality criteria. In various versions, the controller may be integral with, or external to, the air purifier. In various versions, the controller provides the indication to the purifier using wireless communication technology.

In various embodiments, the at least one sensor may include a sensor configured to detect operation of a vacuum cleaner, a sensor configured to detect that the indoor environment has been exposed to an external environment, a sensor configured to detect operation of a kitchen appliance (e.g., a fume hood, an oven, a stove top, etc.), a sensor configured to detect operation of a washer or dryer, and so forth. In some embodiments, the air purifier may be a first air purifier. The at least one sensor may include a sensor configured to detect operation of a second air purifier in an environment external to the indoor environment.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 1 is a schematic depiction of an environment in which an air quality-monitoring system may be deployed, in accordance with various embodiments.

DETAILED DESCRIPTION OF THE EMBODIMENTS

Figure 2:
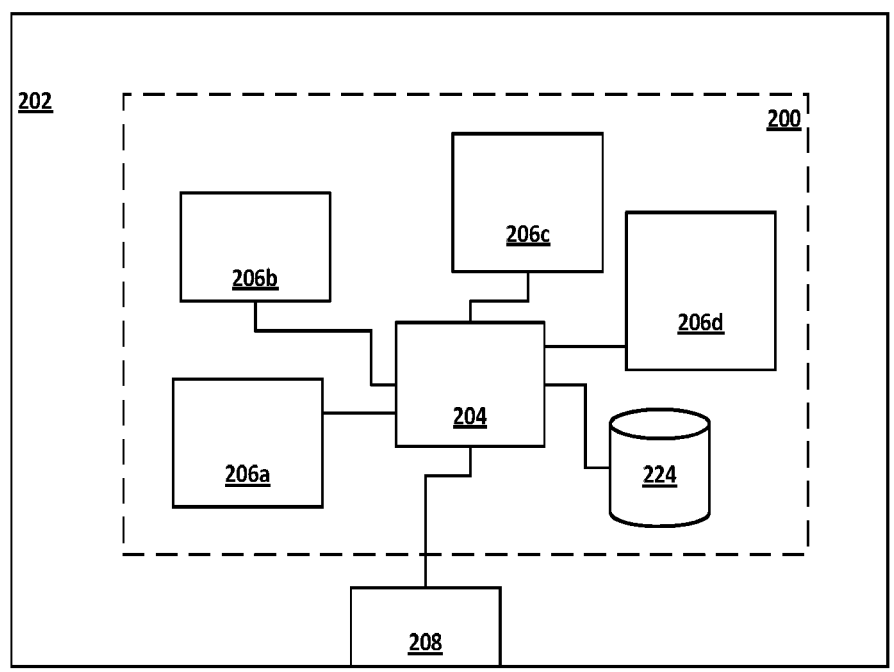
FIG. 2 depicts an alternative embodiment of an air quality-monitoring system that is integral with an air purifier, in accordance with various embodiments.

Air quality in an environment may change before, during, and after various events. For example, in an indoor environment such as an office or one or more rooms of a home or apartment, levels of some types of pollutants may increase when certain appliances (e.g., vacuum cleaners, washers, dryers, stoves, ovens, grills, griddles, microwaves, etc.) are operated. Levels of some types of pollutants may increase when the indoor environment is exposed to an external environment by, for example, a window or door being opened. Some types of pollutants may be present at increased levels when an occupant is performing an activity that may introduce pollutants into the indoor environment, such as smoking, painting, etc. Operating an air purifier without regard to the changes in air quality caused by these various events may lead to overconsumption of power and/or unnecessary wear and tear on the air purifier and/or one or more incorporated air filters. Even operating an air purifier in response to detected changes in air quality caused by these various events may not be sufficient to prevent durations of unacceptable air quality.

Thus, Applicants have recognized a need in the art to enable operation of one or more air purifiers based on occurrence of various events not directly related to air quality. More generally, Applicants have recognized and appreciated that it would be beneficial to operate one or more air purifiers in response to one or more events that likely will cause air quality to decrease to unacceptable levels. In view of the foregoing, various embodiments and implementations of the present invention are directed to air quality-monitoring systems that collect environment and behavioral data, detect operation of one or more mechanisms external to air purifiers, and selectively provide indications that operation of the one or more mechanisms will cause air quality within an indoor environment to become unacceptable.

FIG. 1 is a schematic depiction of an environment in which an air quality-monitoring system 100 configured with selected aspects of the present disclosure may be deployed. Air quality-monitoring system 100 may be in communication (also referred to as "communicatively coupled") with one or more air purifiers 102*a* and 102*b* (each may be referred to generically as "air purifier 102"). Each air purifier 102 may include one or more air filters (not depicted in FIG. 1). Each air filter installed in an air purifier 102 may target one or more pollutants. Pollutants targeted by one air filter may partially overlap and/or be completely disjoint from pollutants targeted by another air filter. As used herein, "pollutants" may refer to various types of particles (e.g., dust, pet hair, dander, etc.), various types of chemicals (e.g., volatile organic compounds, or "VOCs," formaldehyde, BTX, etc.), and so forth. Air quality-monitoring system 100 may include a controller 104, one or more sensors 106*a-e*, and one or more input/output ("I/O") components 108.

Controller 104 may be implemented in numerous ways, such as with dedicated hardware, software, or any combination of the two, to perform various functions discussed herein. A "processor" is one example of a controller which employs one or more microprocessors that may be programmed using software (e.g., microcode) to perform various functions discussed herein. Controller 104 may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various embodiments described herein, controller 104 may be operably and/or communicatively coupled with other components, such as sensors 106*a-e*, I/O component 108, air purifier 102, and so forth, using various wired and/or wireless technologies. In some embodiments, wireless technology such as BlueTooth, Wi-Fi, cellular, RFID, NFC, and other similar technologies may be employed. In other embodiments, wired technology such as wire buses, Ethernet, and so forth, may be employed. I/O component 108 may take various forms, including but not limited to a keyboard, a mouse, a microphone, a touch screen, one or more dipswitches, one or more buttons, one or more knobs, and so forth.

In some embodiments, controller 104 may cause various recommendations to be provided to users, e.g., via I/O component 108, and/or may cause one or more air purifiers 102 to operate in various ways based on one or more signals from sensors 106*a-e* and/or I/O component 108. In some embodiments, controller 104 may cause various features of air purifiers 102, such as one or more fans, one or more installed air filters, one or more mechanisms to block one or more air filters or airstreams, to operate in various ways to target various pollutants. In some embodiments, controller 104 may be configured to transmit one or more indications of poor air quality and/or commands to one or more air purifiers 102. Air purifiers 102 may be configured to interpret those indications and/or commands and take remedial action, such as notifying a user of impending poor air quality (e.g., using one or more I/O components 108 such as LEDs or a display) and/or changing the way air purifiers 102 are operated (e.g., increasing fan speed, etc.) to prevent air quality from deteriorating to unacceptable levels. In some embodiments, controller 104 may make recommendations to users about air purification by transmitting data to a remote computing device operated by a user, such as a smart phone or tablet. Using the smart phone or tablet, the user may view various recommendation data provided by controller 104 in order to make various decisions as to how to operate air purifier 102.

A "sensor" as used herein may refer to a component, implemented with any combination of software and hardware, that is configured to detect various events. Some sensors are configured to detect operation of mechanisms 110 that are external to air purifier 102 (examples will be described below). Other sensors 106 may be configured to detect levels of one or more pollutants. In various embodiments, sensors 106 may be configured to provide signals to controller 104. If a sensor 106 is integral to a unit that also includes controller 104, then the sensor 106 may transmit the signal to controller 104 via one or more buses. If a sensor 106 is external to a unit that includes controller 104, then the sensor 106 may transmit its signal to controller 104 using various wired or wireless communication technologies described above.

Operation of various mechanisms 110 that are external to (e.g., unrelated to) air purifier 102 may affect air quality within an environment if operated. Such mechanisms include but are not limited to a vacuum cleaner 112, kitchen appliances such as an oven/stovetop 114, a microwave 116, a fume hood (not depicted), other appliances such as a washer/dryer 118, a window 120, a door (not depicted), bathroom appliances (not depicted) such as showers (which may create humidity), sinks, hair dryers, etc., and so forth. As noted above, operating air purifier 102 without regard to pollutants raised by operation of such mechanisms, or even operating air purifier 102 in response to changes in air quality caused by operation of these mechanisms, may be inefficient and/or insufficient to avoid unacceptable dips in air quality.

Accordingly, one or more sensors 106 may be configured to detect operation of the various mechanisms (e.g., one or more of 112-120) and to provide signals indicative of such operation to controller 104. In various embodiments, controller 104 may be configured to determine, based on one or more signals from one or more sensors 106, a likelihood that operation of a mechanism (e.g., one or more of 112-120) will cause a measure of air quality within an indoor environment to fail one or more air quality criteria.

"Air quality criteria" may be selected from various sources and/or be based on various information. In some embodiments, one or more air quality criteria may be based on government regulations that set forth acceptable levels of various pollutants in various environments. In other embodiments, one or more criteria may be customized to a particular situation. For example, an asthmatic user may be more sensitive to various pollutants than a non-asthmatic user. The asthmatic user may operate her personal air quality-monitoring system 100, e.g., using I/O component 108, to lower one or more thresholds associated with pollutants to which asthmatics may be sensitive. As another example, an air quality-monitoring system 100 used in a clean room may have heightened standards as to an acceptable level of pollutants.

Based on a likelihood that operation of a mechanism will cause a measure of air quality within an indoor environment to fail one or more air quality criteria, controller 104 may selectively perform various actions that may result in remediation of the impending decrease in air quality. In some embodiments, controller 104 may selectively provide an indication to a user, e.g., via I/O component 108 or via a remote computing device such as a smart phone 122, that operation of one or more mechanisms (e.g., 112-120) will cause air quality within the indoor environment to fail the one or more criteria. Such an indication may come in various audible or visual forms, such as one or more alarms, blinking lights, messages displayed on a touch screen of a remote computing device such as smart phone 122 or a tablet computer, and so forth. In other embodiments, and as noted above, controller 104 may provide the indication to one or more air purifiers 102 using wireless communication technology, and the air purifier 102 may respond by taking various remedial actions.

Sensors 106 may be configured to detect operation of mechanisms external to air purifier 102 in various ways. Some sensors 106, such as a smart home sensor 106a, may be in communication with one or more components of a so-called "smart" home. For example, vacuum cleaner 112, oven/stove 114, microwave 116, washer/dryer 118, air purifier 102, and/or other similar mechanisms may be networked (wirelessly or wired) with one or more smart home controller, such as a smart home "hub," one or more smart phones/tablets/personal computers 122, or even controller 104 itself. When one or more of mechanisms 110 are operated, notifications may be transmitted to smart home sensor 106a, e.g., from the device being operated, a smart home control computer, smart phones/tablets/personal computers 122, and so forth.

In some embodiments, operation of air purifiers 102 themselves may be interpreted by controller 104 as evidence of an impending decrease in air quality. For example, air purifiers 102a and 102b may be in different rooms of a house. Controller 104 may determine, e.g., based on a signal received at smart home sensor 106a, that first air purifier 102a is being operated. Based on this signal, controller 104 may determine that air quality elsewhere in the house, such as in the vicinity of second air purifier 102b, is likely to decrease to below acceptable levels. Controller 104 may take responsive remedial action, such as prompting a user to operate second air purifier 102b, or automatically causing second air purifier 102b to operate.

Other sensors 106 may be configured to detect operation of mechanisms external to air purifier 102 in less direct ways. For example, a noise sensor 106b may be a microphone or other similar device configured to detect pressure waves (e.g., sound). Noise sensor 106b may provide a signal of detected sound to controller 104. Controller 104 may then compare the signal to one or more sound wave profiles associated with operation of one or more mechanisms (e.g., 112-120) external to air purifier 102. If controller 104 determines that the signal from noise sensor 106b matches a sound wave profile, controller 104 may determine that a particular mechanism has been operated, and make take appropriate remedial action. For example, one sound wave profile may be designed to match sound created during operation of vacuum cleaner 112. When controller 104 determines, based on a signal from noise sensor 106b, that vacuum cleaner 112 is being operated, controller 104 may determine a likelihood that a state air quality in the environment is about to transition to unacceptable levels. If the likelihood is sufficiently high, controller 104 may take remedial action (e.g., notify a user using I/O component 108, operate air purifier 102).

In some embodiments, controller 104 may be configured to record one or more sound wave profiles, e.g., periodically and/or over time. Controller 104 may further be configured to monitor air quality, e.g., using pollutant sensors such as first pollutant sensor 106c and second pollutant sensor 106d, periodically and/or over time. In some embodiments, controller 104 may "learn" that certain sound wave profiles are associated with decreases in air quality. Suppose controller 104 detects and logs a series of detected similar increases in a particular pollutant. Suppose further that controller 104 records a similar sound immediately prior to each detected increase in pollutant levels. Controller 104 may determine that whatever caused those similar sounds (e.g., operation of vacuum cleaner 112) also caused the corresponding increases in the particular pollutant. Controller 104 may thereafter associate a sound wave profile that captures the noise with an impending increase in the particular pollutant.

As another example of a less-direct way of detecting operation of a mechanism external to air purifier 102, in some embodiments, controller 104 may infer operation of a mechanism external to air purifier 102 based on signals from multiple sensors 106. Suppose a first pollutant sensor 106c is configured to detect a first pollutant associated with an indoor environment. Suppose further that a second pollutant sensor 106d is configured to detect a second pollutant associated with pollution external to the indoor environment, such as pollution from another room (e.g., outside of a clean room), or pollution typically originating outdoors. A significant and/or sudden decrease in a level of the first pollutant detected contemporaneously with a significant and/or sudden increase in a level of the second pollutant may indicate that the indoor environment has been exposed to an external environment.

Accordingly, in various embodiments, controller 104 may be configured to compare signals from the first and second sensors 106c and 106d. Based on that comparison, controller 104 may determine that a mechanism on the boundary of the indoor environment, such as window 120, has been operated to expose the indoor environment to the external environment. In some embodiments where the exterior environment is outdoors, controller 104 may confirm its determination by comparing one or more levels of pollutants measured in the indoor environment to local air quality index (AQI) measurements obtained from external sources, e.g., via the Internet.

In various embodiments, air quality-monitoring system 100 may calibrate itself to an indoor environment in which it is deployed, so that it can more effectively predict when particular events are likely to cause air quality to decrease to unacceptable levels. In various embodiments, air quality-monitoring system 100 may include a persistent memory 124 (e.g., one or more databases) to store various data that may be considered by controller 104 when making various determinations described herein. In some embodiments, user preference data may be stored in persistent memory 124, and may include data such as a user's preferred air quality criteria for identifying when air quality is unacceptably low (which for instance may be different between asthmatic and non-asthmatic users), data about when the user would like air purifier 102 to operate or not operate, user-input data about the environment (e.g., spatial dimensions, postal code to obtain local weather), and so forth. Persistent memory 124 may additionally or alternatively store historical data about detected levels of pollutants, noise levels (including sound wave profiles mentioned above), and so forth. In some embodiments, such historical data and other data about an environment (observed via one or more sensors or input by a user) may be assembled, e.g., by controller 104, into an air quality profile associated with that particular environment. Every indoor environment may have its own unique air quality profile.

In some embodiments, an air quality profile may include air quality measurements of a particular indoor environment (e.g., a room) after the room has been "ventilated" (e.g., been exposed to an exterior environment, such as outdoors, e.g., by opening window 120). For example, controller 104 may determine levels of pollutants typically associated with outdoor sources each time the room is ventilated. After determining such levels after multiple ventilations over time, controller 104 may calculate various statistics about outdoor pollutant levels present in the indoor environment after ventilation, such as average and/or maximum levels. An air quality profile may additionally or alternatively include other data points, such as average and/or maximum time intervals required for air quality in the indoor environment to return to acceptable levels after being ventilated.

Other information may be stored in persistent memory 124 as well. In some embodiments, persistent memory 124 may be used to store information about characteristics of one or more air purifiers 102. For example, persistent memory 124 may store information about one or more air filters deployed in a given air purifier 102, such as pollutants targeted by air filters, dimensions of air filters, useful life spans of air filters, and so forth. In some embodiments, controller 104 may track how long each air filter has been in use, and may store such usage records in persistent memory 124. Controller 104 may compare an air filter's usage records to its useful life span, and may prompt a user (e.g., using I/O component 108) to change the air filter when its usage records indicate it has surpassed its useful life span.

In some embodiments, controller 104 may be configured to provide the user with information beyond simply instructing the user to operate air purifier 102. This information may be provided by controller 104 at I/O component, at an air purifier 102, or even at a remote computing device such as smart phone 122. For example, controller 104 may recommend that the user change one or more air filters in an air purifier 102, that the user alter the way he or she operates the air purifier 102, that the user alter his or her behavior in the environment in general, and/or that the user replace the current air purifier with a different type of air purifier (e.g., more powerful, targets different pollutants, etc.). To make such recommendations, controller 104 may compare one or more aspects of an air quality profile of a particular environment to one or more characteristics of an air purifier 102, a user's ongoing operation of an air purifier, and other aspects of the user's behavior.

To recommend a new air filter, controller 104 may first compare an air quality profile's historical data relating to pollutants detected in an environment over time to one or more characteristics of an air filter of an air purifier 102 deployed in the environment. Controller 104 may determine that the air filter used in air purifier 102 is not well-suited to capture or otherwise render benign the pollutants that the air quality profile indicates have been historically detected in the environment. Controller 104 may identify one or more alternative air filters that may be used in air purifier 102 instead that are better suited to capture or otherwise render benign pollutants historically detected in the environment. For example, if BTX is historically detected in the environment and the air purifier 102 does not have any air filters installed that target BTX, controller 104 may recommend replacing one or more alternative air filters with an air filter that targets BTX.

In some embodiments, information about alternative air filters may be stored in persistent memory 124, e.g., during manufacture and/or at software updates. In other embodiments, controller 104 may obtain information about alternative air filters in real time from one or more remote computing devices over one or more networks (e.g., the Internet). In some embodiments, controller 104 may be configured to provide a user with various information about alternative air filters, enabling the user to make an informed decision. For example, controller 104 may provide predications of how long it would take after closing a window for the air purifier to reduce a targeted pollutant to an acceptable level using various alternative air filters. In some embodiments, in addition to or instead of recommending an alternative air filter to a user, controller 104 may simply transmit a request to an air filter service provider to ship a suitable alternative air filter to the user.

To recommend an alteration in user operation of air purifier 102, controller 104 may compare various aspects of an air quality profile of an environment to various aspects of a user's operation of an air purifier 102 deployed in that environment over time. Based on that comparison, controller 104 may make one or more recommendations to the user as to how the user can alter the way he or she operates air purifier 102 to better alleviate air quality concerns. If a particular pollutant is historically detected in an environment at a particular time of day and the user doesn't typically operate the air purifier 102 at that time, controller 104 may recommend that the user begin running the air purifier 102 during that time of day. If the environment historically is humid and the user has the air purifier set to operate as though the environment is dry, controller 104 may recommend that the user alter his or her operation of air purifier 102 so that it operates in a "humid" mode. Other changes in user operation of an air purifier 102 that may be recommended by controller 104 may include but are not limited increasing frequency of use of the air purifier 102, aligning the usage times of the air purifier 102 with other devices, such as an air conditioner and/or a humidifier, and so forth.

In some embodiments, controller 104 may recommend that a user alter his or her behavior generally separate from operation of air purifier 102. For example, controller 104 may compare various aspects of an air quality profile of an environment to various aspects of a user's general behavior (e.g., cooking patterns, smoking, opening and closing of windows to ventilate the environment, etc.) in the environment over time. Based on that comparison, controller 104 may make one or more recommendations to the user as to how the user can alter his or her general behavior to better alleviate air quality concerns. For example, controller 104 may recommend that the user reduce a time of ventilation (i.e., keep windows open for a shorter amount of time), avoid ventilation during peak outdoor pollution times (e.g. rush hour), or increase ventilation during peak indoor pollution times (e.g., while cooking, vacuum cleaning, smoking, etc.).

Recommending replacement of an air purifier 102 (e.g., an upgrade) may work similarly to recommending replacement of an air filter. Controller 104 may first compare an air quality profile's historical data relating to pollutants detected in an environment (and/or to one or more characteristics of the environment) over time to one or more characteristics of an air purifier 102 deployed in the environment. Controller 104 may determine that the air purifier 102 is not well-suited to capture or otherwise render benign the pollutants (or levels of pollutants) that the air quality profile indicates have been historically detected in the environment. Controller 104 may identify on or more alternative air purifiers that may be used instead that are better suited to capture or otherwise render benign pollutants (or levels of pollutants) historically present in the environment.

In some embodiments, controller 104 may be configured to predict, based on changes in detected pollutant levels over time, a likelihood that a measure of air quality within an indoor environment will soon to fail one or more air quality criteria. In some embodiments, if a rate of change observed by controller 104 in levels of the detected pollutant satisfies one or more thresholds, controller 104 may take various remedial actions, such as preemptively operating an air purifier 102 to avoid bad air quality. For instance, a gradual (e.g., constant) increase in a detected level of a particular pollutant may be natural, even unavoidable, as few indoor environments are truly hermetically sealed from other environments. By contrast, if a rate of change of the pollutant increases suddenly, that may evidence occurrence of an intervening event, such as running of a vacuum 112, that may raise levels of that pollutant suddenly. In the latter instance, and even where a level of the pollutant is not yet in violation of some criterion, controller 104 may determine a likelihood that the level of the pollutant will become unacceptable, and may selectively and preemptively cause air purifier 102 to take remedial action.

FIG. 2 depicts an alternative air quality-monitoring system 200 with many components similar to those found in air quality-monitoring system 100 of FIG. 1, including a controller 204, various sensors 206a-d, I/O component 208, and persistent memory 224. Unlike in FIG. 1, where air quality-monitoring system 100 was separate from, but in network communication with, one or more air purifiers 102a and 102b, air quality-monitoring system 200 is integral with air purifier 202. While sensors 206a-d are depicted as being integral with air quality-monitoring system 200, this is not meant to be limiting. In embodiments like air quality-monitoring system 100 of FIG. 1 and air quality-monitoring system 200 of FIG. 2, one or more sensors may be located elsewhere, e.g., as part of a smart home hub, on a computing device such as smart phone 122, within another device such as a smoke detector, a carbon monoxide detector, stand-alone, and so forth.

Figure 3:
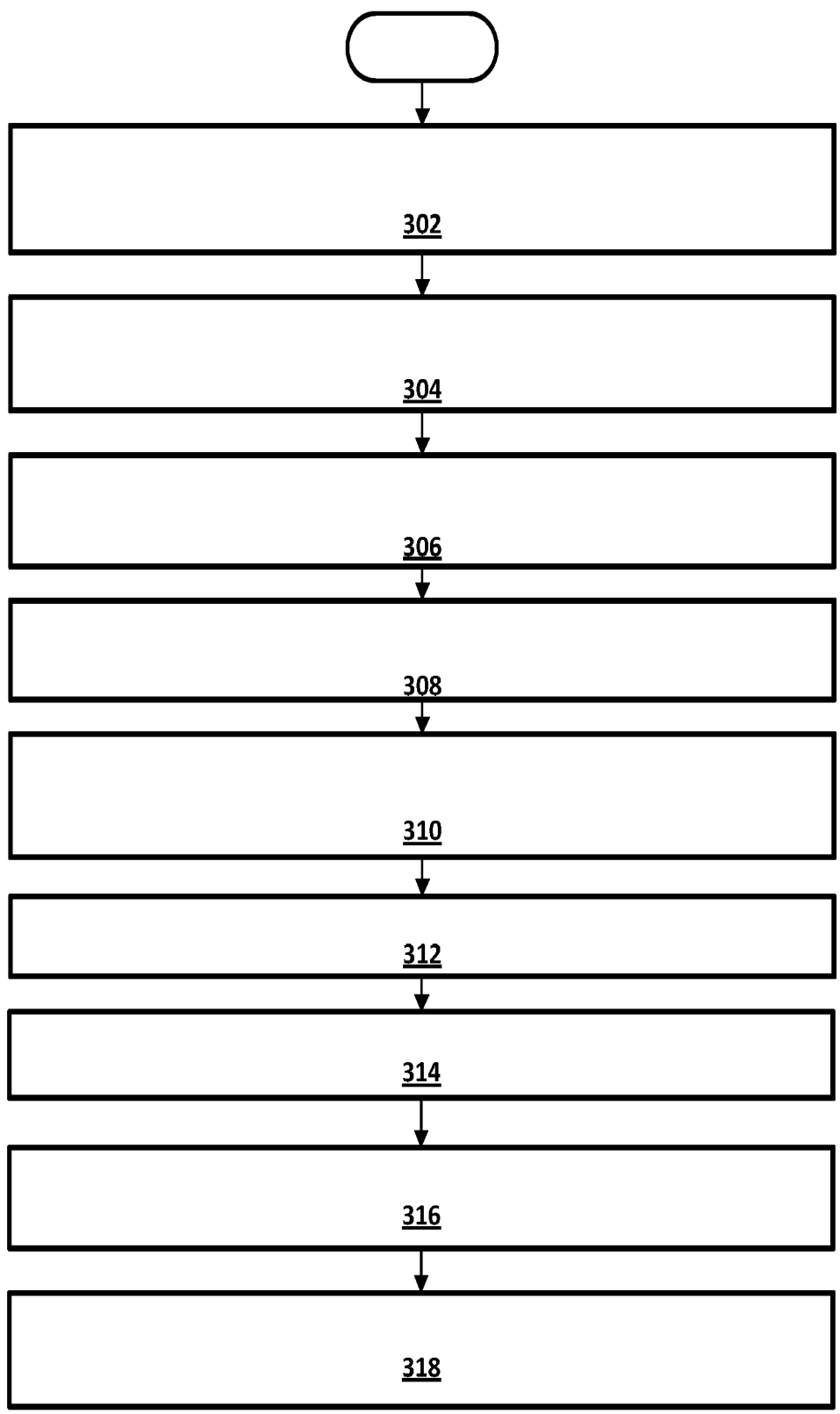
FIG. 3 depicts an example method of collecting environment, behavioral, and air quality data, and making one or more recommendations to a user.

FIG. 3 depicts an example method 300 of building an air quality profile associated with a particular indoor environment, collecting data about user operation of one or more air purifiers and user behavior in general, analyzing this information to determine likelihoods that particular activities will affect air quality in the environment negatively, and making suitable recommendations, in accordance with various embodiments. Various operations of method 300 may be performed by various components, such as one or more sensors (106, 206) or a controller (104, 204). For the sake of brevity and convenience, operations will be described as generally being performed by a "system." While operations are depicted in a particular order, this is not meant to be limiting. One or more operations may be reordered, added, or omitted, and one or more operations may be performed simultaneously.

At block 302, the system may store levels of one or more indoor pollutants detected over a time period. For example, after an air quality-monitoring system such as 100 or 200 is installed in an apartment, the system may take periodic readings using one or more pollutant sensors (e.g., 106c, 106d, 206c, 206d). At block 304, the system may store one or more levels of outdoor pollutants detected in the environment after a ventilation. At block 306, the system may store one or more indications of lengths of time required after ventilation of the environment to reduce outdoor pollutants detected in the environment to acceptable levels.

At block 308, the system may collect and/or store data about the environment in persistent memory. For example, a user may provide (e.g., via I/O component 108 or via smart phone 122) attributes about the environment such as its spatial dimensions, how many windows/doors it has, how much furniture is present, and so forth. Additionally or alternatively, the system may determine one or more attributes of the environment by, for instance, recording humidity over time, recording attributes of the user's interaction with the environment over time (e.g., how often does the user ventilate, cook, etc.). Information collected at blocks 302-308 may collectively form an air quality profile of the environment.

At block 310, the system may store indications of user operation of an air purifier (e.g., 102, 202) over the same time period as block 302. For example, the system may track when the user operates the air purifier, for how long the user operates the air purifier at a time, one or more settings of the air purifier while in operation, and so forth. At block 312, the system may store indications of user behavior in general over the same time period as blocks 302 and 310. For example, the system may track how often the user ventilates the environment, for how long the user ventilates the apartment, when the user operates various pollutant-raising devices such as a vacuum cleaner or dryer, and so forth. At block 314, the system may collect data about the air purifier used in the environment, such as attributes of one or more air filters, capabilities of the air purifier, etc.

At block 316, the system may compare data collected at one or more of blocks 302-308 (i.e., an air quality profile of the environment) to data collected at one or more of blocks 310-314 (i.e., information about user operation of an air purifier, user behavior in general, and information about the air purifier). At block 318, the system may, based on the comparison of block 316, make one or more recommendations to the user as to how the user can better address air quality concerns within the environment. For example, the system may recommend that the user change one or more air filters, replace an air purifier, operate an air purifier differently, or alter the user's other behavior within an environment.

Figure 4:
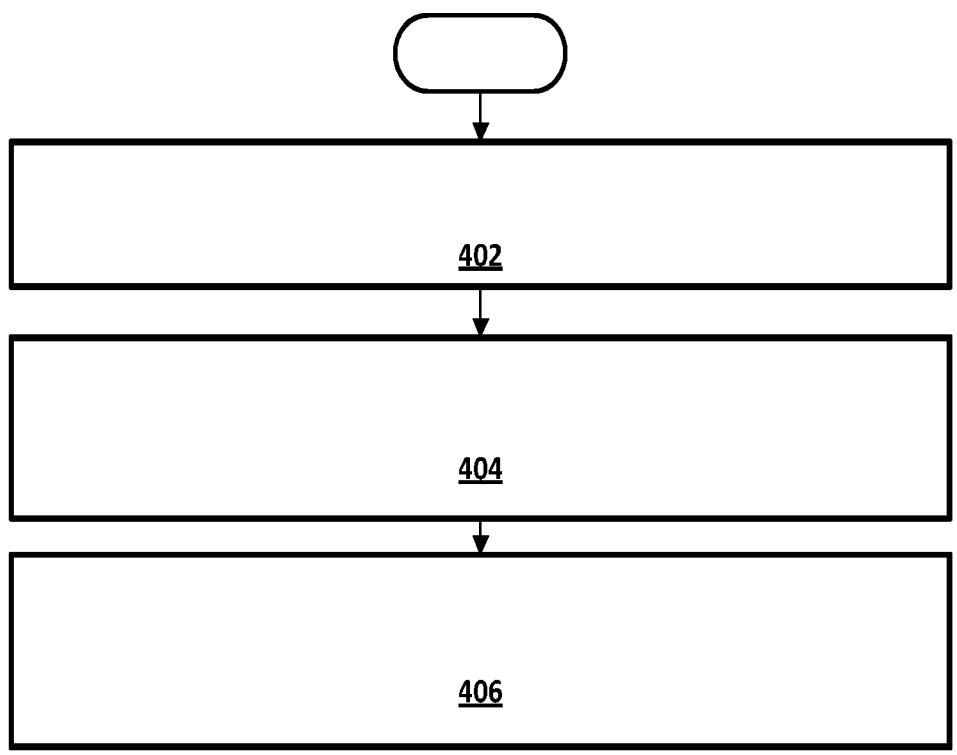
FIG. 4 depicts an example method for monitoring air quality, in accordance with various embodiments.

FIG. 4 depicts an example method 400 that may be performed by the system to address air quality concerns in real time, in accordance with various embodiments. At block 402, the system may detect operation of a mechanism within or at a boundary of an indoor environment. As noted previously, the mechanism may come in various forms (see 112-120 in FIG. 1), and its operation may be detected in various ways by various types of sensors. At block 404, the system may determine a likelihood that operation of the mechanism will cause a measure of air quality within the indoor environment to fail one or more air quality criteria. Air quality criteria may be selected based on government regulations, needs of particular users (e.g., asthmatics), and so forth.

At block 406, the system may selectively provide, based on the likelihood, an indication that operation of the mechanism will cause the measure of air quality within the indoor environment to fail the one or more air quality criteria. For instance, the system may provide output to the user to prompt the user to make some change to the air purifier or the manner in which the user operates it. Additionally or alternatively, the system may provide an indication to the air purifier itself, and the air purifier itself may automatically take responsive remedial action.

Figure 5:
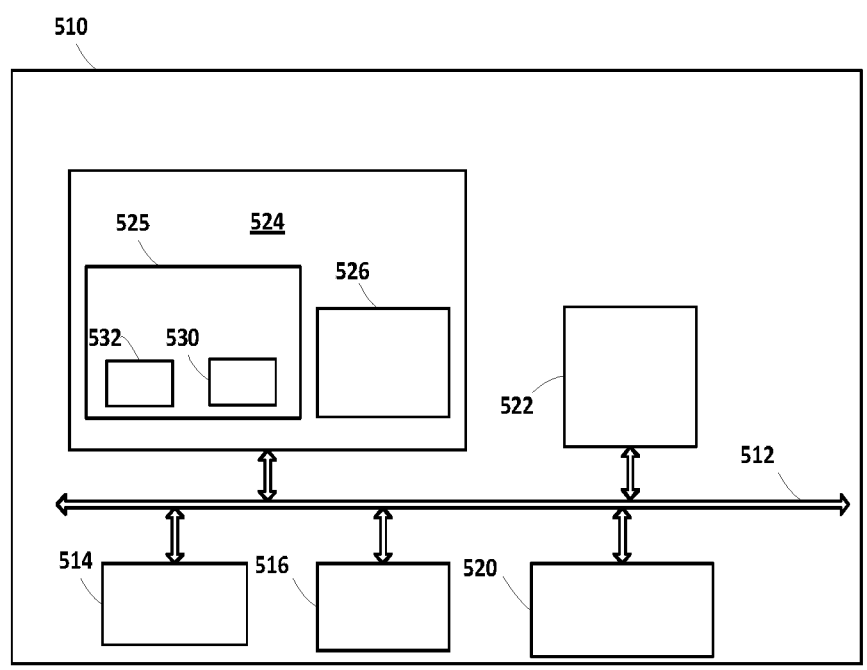
FIG. 5 depicts a block diagram of an example computer system, in accordance with various embodiments.

FIG. 5 is a block diagram of an example computer system 510. Computer system 510 typically includes at least one processor 514 which communicates with a number of peripheral devices via bus subsystem 512. These peripheral devices may include a storage subsystem 524, including, for example, a memory subsystem 525 and a file storage subsystem 526, user interface output devices 520, user interface input devices 522 (in some embodiments, 520 and 522 may collectively form I/O component 108 or 208), and a network interface subsystem 516. The input and output devices allow user interaction with computer system 510. Network interface subsystem 516 provides an interface to outside networks and is coupled to corresponding interface devices in other computer systems.

User interface input devices 522 may include a keyboard, pointing devices such as a mouse, trackball, touchpad, or graphics tablet, a scanner, a touchscreen incorporated into the display, audio input devices such as voice recognition systems, microphones, and/or other types of input devices. In general, use of the term "input device" is intended to include all possible types of devices and ways to input information into computer system 510 or onto a communication network.

User interface output devices 520 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term "output device" is intended to include all possible types of devices and ways to output information from computer system 510 to the user or to another machine or computer system.

Storage subsystem 524 stores programming and data constructs that provide the functionality of some or all of the modules described herein. For example, the storage subsystem 524 may include the logic to perform selected aspects of methods 300 and/or 400, as well as to implement one or more aspects of controller 104 or 204, one or more sensors 106 or 206, and so forth.

These software modules are generally executed by processor 514 alone or in combination with other processors. Memory 525 used in the storage subsystem 524 can include a number of memories including a main random access memory (RAM) 530 for storage of instructions and data during program execution and a read only memory (ROM) 532 in which fixed instructions are stored. A file storage subsystem 526 can provide persistent storage (e.g., 124) for program and data files, and may include a hard disk drive, a floppy disk drive along with associated removable media, a CD-ROM drive, an optical drive, or removable media cartridges. The modules implementing the functionality of certain implementations may be stored by file storage subsystem 526 in the storage subsystem 524, or in other machines accessible by the processor(s) 514.

Bus subsystem 512 provides a mechanism for letting the various components and subsystems of computer system 510 communicate with each other as intended. Although bus subsystem 512 is shown schematically as a single bus, alternative implementations of the bus subsystem may use multiple busses.

Computer system 510 can be of varying types including a workstation, server, computing cluster, blade server, server farm, or any other data processing system or computing device. Due to the ever-changing nature of computers and networks, the description of computer system 510 depicted in FIG. 5 is intended only as a specific example for purposes of illustrating some implementations. Many other configurations of computer system 510 are possible having more or fewer components than the computer system depicted in FIG. 5.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of" when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An air quality-monitoring system, comprising:
   at least one sensor configured to detect operation of a mechanism within or at a boundary of an indoor environment, wherein the mechanism is external to an air purifier associated with the indoor environment;
   a persistent memory for storing data about the indoor environment observed by the at least one sensor;
   a controller, integral to said air purifier, communicatively coupled with the at least one sensor, said controller configured to:
   assemble the data into an air quality profile associated with said indoor environment;
   determine, based on a signal from the at least one sensor and on the air quality profile, a likelihood that operation of the mechanism will cause a measure of air quality within the indoor environment to fail one or more air quality criteria;
   selectively provide, based on the likelihood, an indication that operation of the mechanism will cause the measure of air quality within the indoor environment to fail the one or more air quality criteria; and
   cause the air purifier to take remedial action to prevent the measure of air quality within the indoor environment from failing the one or more air quality criteria.

2. The air quality-monitoring system of claim 1, wherein the controller provides the indication to the air purifier using wireless communication technology.

3. The air quality-monitoring system of claim 1, wherein the at least one sensor includes a sensor configured to detect operation of a vacuum cleaner.

4. The air quality-monitoring system of claim 1, wherein the at least one sensor includes at least one sensor configured to detect that the indoor environment has been exposed to an external environment.

5. The air quality-monitoring system of claim 4, wherein the at least one sensor comprises a first sensor to detect a first pollutant associated with the indoor environment and a second sensor to detect a second pollutant associated with pollution external to the indoor environment, and wherein the controller is configured to determine, based on a comparison of signals from the first and second sensors, that a mechanism on the boundary of the indoor environment has been operated to expose the indoor environment to the external environment.

6. The air quality-monitoring system of claim 5, wherein the second pollutant is associated with outdoor pollution, and the external environment is outdoors.

7. The air quality-monitoring system of claim 1, wherein the at least one sensor includes a sensor configured to detect operation of a kitchen appliance.

8. The air quality-monitoring system of claim 7, wherein the kitchen appliance comprises at least one of: a fume hood, an oven, and a stove top.

9. The air quality-monitoring system of claim 1, wherein the at least one sensor includes a sensor configured to detect operation of at least one of: a washer and dryer.

10. The air quality-monitoring system of claim 1, wherein the air purifier is a first air purifier, and wherein the at least one sensor includes a sensor configured to detect operation of a second air purifier in an environment external to the indoor environment.

11. A computer-implemented method of monitoring and maintaining air quality, comprising:
   detecting, by at least one sensor, operation of a mechanism within or at a boundary of an indoor environment, wherein the mechanism is external to an air purifier associated with the indoor environment;
   determining, by a controller, integral to the air purifier, based on a signal received by the controller from the at least one sensor, a likelihood that operation of the mechanism will cause a measure of air quality within the indoor environment to fail one or more air quality criteria;
   selectively provide, based on the likelihood, an indication that operation of the mechanism will cause the measure of air quality within the indoor environment to fail the one or more air quality criteria; and
   cause the air purifier to take remedial action to prevent the measure of air quality within the indoor environment from failing the one or more air quality criteria.

12. An air quality-monitoring system, comprising:
   at least one sensor configured to detect an air quality within or at a boundary of an indoor environment;
   a persistent memory for storing data about the indoor environment observed by the at least one sensor;
   a controller, remote from communicatively coupled with the at least one sensor and configured to:
   assemble the data into an air quality profile associated with that environment;
   determine, based on a signal from the at least one sensor and on the air quality profile, a likelihood a measure of air quality within the indoor environment fails one or more air quality criteria.

13. The air quality-monitoring system of claim 12, wherein the at least one sensor includes a sensor configured to detect operation of an appliance.

14. The air quality monitoring system of claim 13, wherein the appliance is one of: a vacuum cleaner, a fume hood, an oven, a stove top, a washer and dryer.

15. The air quality monitoring system of claim 12, further comprising:
   a second sensor said second sensor configured to measure an air quality of an outside atmosphere, wherein said measured air quality of said outside atmosphere is provided to said controller, wherein said controller is configured to:
   cause the air purifier to take remedial action to prevent the measure of air quality within the indoor environment from failing the one or more air quality criteria based on the measure air quality of said outside atmosphere.

* * * * *